(12) United States Patent
Yermiyahu et al.

(10) Patent No.: US 12,372,485 B2
(45) Date of Patent: Jul. 29, 2025

(54) DEVICE FOR MEASURING ELEMENT CONCENTRATIONS IN PLANT LEAVES AND METHOD OF IMPLEMENTING THE SAME

(71) Applicant: The State of Israel, Ministry of Agriculture & Rural Development, Agricultural Research Organization (ARO) (Volcani Center), Rishon Lezion (IL)

(72) Inventors: Uri Yermiyahu, Yavne (IL); Zeev Schmilovitch, Yehud (IL); Victor Alchanatis, Mazkeret Batya (IL); Tal Rapaport, Lehavim (IL)

(73) Assignee: The State of Israel, Ministry of Agriculture & Rural Development, Agricultural Research Organization (ARO) (Volcani Institute), Rishon Lezion (IL)

( * ) Notice: Subject to any disclaimer, the term of this patent is extended or adjusted under 35 U.S.C. 154(b) by 77 days.

(21) Appl. No.: 17/829,936

(22) Filed: Jun. 1, 2022

(65) Prior Publication Data
US 2022/0365009 A1    Nov. 17, 2022

Related U.S. Application Data

(63) Continuation of application No. PCT/IL2020/051251, filed on Dec. 3, 2020.
(Continued)

(51) Int. Cl.
*G01N 23/223*    (2006.01)
*G01N 21/3563*    (2014.01)
(Continued)

(52) U.S. Cl.
CPC ....... *G01N 23/223* (2013.01); *G01N 21/3563* (2013.01); *G01N 21/68* (2013.01);
(Continued)

(58) Field of Classification Search
CPC .. G01N 23/223; G01N 21/3563; G01N 21/68; G01N 21/84; G01N 33/0098;
(Continued)

(56) References Cited

U.S. PATENT DOCUMENTS

2011/0087470 A1    4/2011    Hames et al.
2014/0046641 A1    2/2014    Hames et al.
(Continued)

FOREIGN PATENT DOCUMENTS

CN    103852481 A    6/2014
CN    104020127 A    9/2014
(Continued)

OTHER PUBLICATIONS

Comino et al., Near-infrared spectroscopy and X-ray fluorescence data fusion for olive leaf analysis and crop nutritional status determination, Jun. 19, 2018, Talanta, vol. 188, pp. 676-684. (Year: 2018).*

(Continued)

*Primary Examiner* — Carolyn Fin
(74) *Attorney, Agent, or Firm* — The Roy Gross Law Firm, LLC; Roy Gross

(57) ABSTRACT

A method of measuring element concentration in plant leaves comprises steps of: (a) gathering leaves of plants to be tested; (b) conditioning specimens of said leaves; (c) obtaining raw count-per-second XRF datasets of said specimens; (d) obtaining raw NIR datasets of said specimens; (e) obtaining raw analytical datasets; and (f) assessing concentrations of minerals within said specimens on the basis of said count-per-second XRF, NIR and analytical datasets.

(Continued)

The aforesaid method further comprises steps of obtaining white reference radiance datasets and normalizing said raw NIR datasets on the basis thereof and providing NIR reflectance datasets.

11 Claims, 12 Drawing Sheets
(11 of 12 Drawing Sheet(s) Filed in Color)

Related U.S. Application Data

(60) Provisional application No. 62/943,816, filed on Dec. 5, 2019.

(51) Int. Cl.
  *G01N 21/68* (2006.01)
  *G01N 21/84* (2006.01)
  *G01N 33/00* (2006.01)

(52) U.S. Cl.
  CPC ......... *G01N 21/84* (2013.01); *G01N 33/0098* (2013.01); *G01N 2021/8466* (2013.01); *G01N 2223/076* (2013.01)

(58) Field of Classification Search
  CPC ..... G01N 2021/8466; G01N 2223/076; G01N 21/31; G01N 21/359
  See application file for complete search history.

(56) References Cited

U.S. PATENT DOCUMENTS

| | | | |
|---|---|---|---|
| 2015/0168364 A1 | 6/2015 | McKinney et al. | |
| 2017/0122889 A1 | 5/2017 | Weindorf et al. | |
| 2022/0196578 A1* | 6/2022 | Pitta' | G01N 35/00613 |
| 2022/0334057 A1* | 10/2022 | Weindorf | G01N 23/2206 |
| 2023/0053268 A1* | 2/2023 | Garcia, Jr. | G06V 20/52 |

FOREIGN PATENT DOCUMENTS

| | | | | |
|---|---|---|---|---|
| CN | 104198396 A | 12/2014 | | |
| CN | 107421894 A | 12/2017 | | |
| CN | 108663330 A | 10/2018 | | |
| EP | 4163620 A1 * | 4/2023 | ............ | A01D 33/08 |
| WO | 2015195988 A1 | 12/2015 | | |

OTHER PUBLICATIONS

Neuwirthová et al., The Effect of Leaf Stacking on Leaf Reflectance and Vegetation Indices Measured by Contact Probe during the Season, May 24, 2017, Sensors, vol. 17, pp. 1-23. (Year: 2017).*
Sapkota et al., Portable X-Ray Fluorescence Spectroscopy for Rapid and Cost-Effective Determination of Elemental Composition of Ground Forage, Mar. 19, 2019, Frontiers in Plan Science, pp. 1-9. (Year: 2019).*
USGS Fact Sheet "Elemental Analysis Using a Handheld X-Ray Fluorescence Spectrometer" Published Jun. 2016, pp. 1-2. Fact Sheet [online]. [Retrieved Jun. 1, 2024]. Retrieved from the internet:<URL:https://pubs.usgs.gov/fs/2016/3043/fs20163043.pdf>. (Year: 2016).*
Comino, Francisco & Cañada, Maria & Aranda, V. & Díaz, A. & Dominguez-Vidal, Ana. (2018). Near-infrared spectroscopy and X-ray fluorescence data fusion for olive leaf analysis and crop nutritional status determination. Talanta. 188. doi: 10.1016/j.talanta.2018.06.058.
PCT International Search Report for International Application No. PCT/IL2020/051251, mailed Feb. 4, 2021, 6pp.
PCT Written Opinion for International Application No. PCT/IL2020/051251, mailed Feb. 4, 2021, 4pp.
Extended European Search Report for European Patent Application No. 20895470.1, dated Dec. 21, 2022, 13pp.
Sapkota et al. (2019). Portable X-ray fluorescence spectroscopy for rapid and cost-effective determination of elemental composition of ground forage. Front Plant Sci. Mar. 19, 2019;10:317. doi: 10.3389/fpls.2019.00317. PMID: 30941156; PMCID: PMC6433940.
Feng et al. (2019). Rapid detection of cadmium and its distribution in Miscanthus sacchariflorus based on visible and hear-infrared hyperspectral imaging. Sci Total Environ. Apr. 1, 2019;659:1021-1031. doi: 10.1016/j.scitotenv.2018.12.458. Epub Jan. 2, 2019. PMID: 31096318.
Rotbart et al. (2013). Estimating olive leaf nitrogen concentration using visible and near-infrared spectral reflectance. Biosystems Engineering, vol. 114, Issue 4,2013, pp. 426-434, ISSN 1537-5110, https://doi.org/10.1016/j.biosystemseng.2012.09.005.
Cordon et al. (2018). Arsenic effects on some photophysical parameters of Cichorium intybus under different radiation and water irrigation regimes. Chemosphere. Aug. 2018;204:398-404. doi: 10.1016/j.chemosphere.2018.04.048. Epub Apr. 10, 2018. PMID: 29677647.
Abdel-Rahman et al. (2010). Estimation of sugarcane leaf nitrogen concentration using in situ spectroscopy. International Journal of Applied Earth Observation and Geoinformation, vol. 12, Supplement 1, 2010, pp. S52-S57, ISSN 1569-8432, https://doi.org/10.1016/j.jag.2009.11.003.
Jaiswal et al. (2016). Synchrotron based high throughput screening method for mineral analysis in cereal and pulse grains meal. Microchemical Journal, vol. 126, 2016, pp. 509-514, ISSN 0026-265X, https://doi.org/10.1016/j.microc.2016.01.011.
Wissmann, Dirk (2019). XRF in Agronomy Applications—Analysis of Plant Tissues and Fertilizers. Spectroscopy. Solutions for Materials Analysis, vol. 34, Issue 11, 11pp.
Gjoka, Xhorxhi, "Combined Protein A and size exclusion high performance liquid chromatography for the single-step measurement of mAb, aggregates and host cell proteins", Journal of Chromatography B, 972, pp. 48-52. doi: 10.1016/j. jchromb.2014.09.017. Epub Sep. 30, 2014. PMID: 25310707.
Chinese Office Action for Chinese Patent Application No. 202080095368.4, dated Jan. 21, 2025, 22pp.

* cited by examiner

DEVICE FOR MEASURING ELEMENT CONCENTRATIONS IN PLANT LEAVES AND METHOD OF IMPLEMENTING THE SAME

CROSS REFERENCE TO RELATED APPLICATIONS

This application is a Bypass Continuation of PCT Patent Application No. PCT/IL2020/051251 having International filing date of Dec. 3, 2020, which claims the benefit of priority of U.S. Provisional Patent Application No. 62/943,816, filed Dec. 5, 2019, the contents of which are all incorporated herein by reference in their entirety.

FIELD OF THE INVENTION

The present invention relates to digestion-based analytical methods of quantifying both essential and non-essential element concentrations in plant leaves and, more particularly, to a quantification method based on a combination of energy-dispersive X-ray fluorescence (EDXRF) spectrometry and near infrared (NIR) spectrometry.

BACKGROUND OF THE INVENTION

With the ongoing and predicted changes in global climate and the continuous growth of human population, the demand to increase sustainable and nutritious food production is greater than ever. Consequently, the optimization of fertilization management becomes an even more important and pressing issue, as a deficiency or excess in various soil elements can limit plant growth and development, impair the yield, quality and safety of agricultural products, and contribute to soil and groundwater degradation. In order to tackle this challenge, it is imperative that the quantification of plant macro- and micronutrients in the field is based on quick, accurate, broad, simple, and affordable methods. While laboratory, digestion-based analytical techniques are considered to be the common and most reliable way of assessing elements status, they are also lengthy, laborious, costly, and hazardous; this is because such procedures depend on proficient manpower to perform extensive weighing, long digestions using various dangerous reagents (such as nitric-, hydrochloric-, perchloric-, sulfuric-, and hydrofluoric acids), and rather expansive spectral analyses with benchtop instruments. Furthermore, in times of high throughputs or when the elements of interest require different digestive approaches, the delays of routine analytical labs become longer and create inevitable bottlenecks—significantly hindering the transfer of recommendations back to the farmer and limiting the sample size that can be analyzed. Apart from these issues, it is also noteworthy that 'wet chemistry'-based methods might prove imprecise due to element volatilization and incomplete matrix solubility, might vary greatly among labs due to a wide array of working protocols, and might be unsuitable for the analysis or re-analysis of limited-size samples due to their inherent destructive nature.

A feasible solution to the abovementioned problems is the use of X-ray fluorescence (XRF) spectrometry, which offers an accurate, reliable, rapid, and non-destructive way to quantify numerous elements. In an XRF system, a highly energized radiation (typically 5-100 keV) is used for ionizing the atoms of a sample, causing the ejection of inner-orbital electrons and, thus, creating vacancies that are almost instantly ($10^{-16}$ s) filled by electrons from outer shells. As the latter are more energetic than electrons of inner orbits, the stabilization of the ionized atom back to its ground state is accompanied by a release of fluorescence photons (i.e., radiative transitions), each of an energy is unique to the relocation between specific energy levels. By identifying a few intense transitions out of all possible ones and measuring the energy of their respective photons, benchtop energy-dispersive XRF (EDXRF) spectrometers can distinguish between elements from sodium (Na) to uranium (U) and quantify their concentrations precisely, in a matter of minutes, without the need for weighing or chemical digestions, and in a non-destructive fashion that allows the storage and re-analysis of samples. In light of these advantages, such instruments have become one of the most widely used X-ray methods in analytical labs since their introduction in the 1970's, being continuously applied in scientific studies of various disciplines. Moreover, thanks to their ability to present accuracies of tenths of a percent for most atomic numbers (Z) and to detect low part-per-million (ppm) levels, benchtop EDXRF devices have also been successful in assessing different element levels in the leaves of numerous plant species.

Despite their promising capabilities, it is important to note that benchtop XRF spectrometers are, by definition, immobile and problematic to convey or be used in field analyses, rather complicated to operate, and still quite expensive to purchase and maintain. In addition, those instruments producing radiation using a tube generally require a relatively long time to stabilize prior to the first measurement, whereas those relying on radioactive isotopes emit continuously and, therefore, require permits and pose additional difficulties for transporting, storing, and maintaining. The vast technological advancements of the last twenty years have, however, enabled the miniaturization of tubes and dramatically promoted X-ray detectability—leading to the creation of portable EDXRF (pEDXRF) instruments that are even smaller, simpler, faster, safer, and cheaper. Furthermore, such tools can perform in situ investigations and be directly presented to the sample, and may be just as accurate as their lab-based counterparts in assessing certain elements within leaves. In this regard, while current pEDXRF spectrometers have the potential to track many essential- and non-essential plant nutrients, including phosphorus (P) and potassium (K), they are also insensitive to important lighter atoms such as nitrogen (N) and boron (B) because the fluorescence yield of Z<magnesium (Mg) is too low to be separated from the background radiation. Interestingly, although it is theoretically easier to quantify heavier elements using XRF, their absolute low quantity in leaves—i.e., a concentration that may be considered adequate or excessive from a plant nutrition perspective, yet resides below the spectrometer's limit of detection—can still result in unsatisfactory signal-to-noise ratios (SNR) and prevent the detection of some essential micro-elements.

In order to provide a more complete picture of macro-nutrients, pEDXRF systems may be combined with portable near infrared (NIR) technology, which has been demonstrated to have a great potential for N assessment in plants throughout the last decades—together with other important bio-chemical properties as the leaf content of water, protein, starch, sugar and oil. Unlike the aforementioned element, fluorescence-based analysis of highly energetic X-rays, NIR spectrometry relies mostly on measuring the reflectance of a non-ionizing and less energetic radiation (700-2500 nm), which causes overtone molecular vibrations at certain spectral bands upon absorption. While the general locations of N-related overtones are known, the use of specific leaf or plant-oriented wavelengths within them is necessary for an accurate inferring of actual concentrations; namely, as the detected NIR radiation profile is strongly affected by the physio-chemical properties of the material, mostly water content and histology, in the case of leaves—they should be calibrated to each other. The same principal is also valid for XRF spectrometry, in which the relationship between measured intensities and element concentrations depends strongly on the matrix composition, which is vastly different among leaves and other materials. Whereas commonly used statistical tools are not apt for targeting those leaf-specific wavelengths, advanced multivariate, chemometric methods are very suitable. Particularly, the partial least squares regression (PLSR) technique is especially useful for reducing the dimensionality of hyperspectral datasets (containing hundreds of wavelengths) such as the XRF and NIR spectra into only the most useful and uncorrelated wavelengths.

To conclude, the aim of the current patent specifications document is to demonstrate the advantage of a combined XRF-NIR-PLSR system in monitoring the majorly-acquired N, P and K elements in particular and other major- and minor-essential nutrients in general, including Mg, sulfur (S), chlorine (Cl), calcium (Ca), manganese (Mn), iron (Fe) and zinc (Zn), using various plant species and sample preparation forms.

F. Comino et al. (Talanta, 188 (2018), 676-684) reports results of leaf analysis directed to diagnosing the nutritional status of the olives. The proposed method is based on a combined use of NIR and portable EDXRF. The ability of both techniques individually and applying two strategies of data fusion for the prediction of the most important plant nutrients, namely N, P, K, Ca, Mg, Mn, Zn, and boron (B) was tested. Predictive models were constructed using PLSR to correlate the spectra with the nutrient contents. Models of unequal prediction performance were obtained for the different parameters when considering both techniques separately Recently, F. comino et al. (ref) demonstrated the potential of combining the abovementioned technologies for mineral quantification of olive leaves. However, their inadequate data processing techniques and use of an interior air atmosphere (see the section 'Detailed Description of the Invention') led to results inferior to those presented in the current document.

SUMMARY OF THE INVENTION

It is hence one object of the invention to disclose a method of measuring element concentration in plant leaves. The aforesaid method comprises steps of: (a) gathering leaves of plants to be tested; (b) conditioning specimens of said leaves; (c) obtaining raw count-per-second XRF datasets of said specimens; (d) obtaining raw NIR datasets of said specimens; (e) obtaining analytical datasets; (f) assessing concentrations of minerals within said specimens on the basis of said count-per-second XRF, NIR and analytical datasets.

It is a core purpose of the invention to provide the method further comprising steps of obtaining white reference radiance datasets and normalizing said raw NIR datasets on the basis thereof and providing NIR reflectance datasets.

Another object of the invention is to disclose the step of conditioning specimens of said leaves comprising dust washing of said leaves, grinding said leaves, drying ground leaves, weighing dried leaves and chemically digesting said dried leaves.

A further object of the invention is to disclose the step of assessing concentrations of minerals comprising a step of preprocessing normalized NIR datasets.

A further object of the invention is to disclose the step of obtaining raw count-per-second XRF datasets of said specimens performed by means of an XRF spectrometer.

A further object of the invention is to disclose the step of obtaining raw NIR datasets of said specimens performed by means of a NIR spectrometer.

A further object of the invention is to disclose the step of obtaining analytical datasets performed by an atomic emission spectrometer.

A further object of the invention is to disclose the step of obtaining analytical datasets performed by an inductively coupled plasma optical emission spectrometer.

A further object of the invention is to disclose the step of assessing concentrations of minerals within said specimens comprising a mineral selected from the group consisting of Magnesium, Phosphorus, Sulfur, Chlorine, Potassium, Calcium, Manganese, Iron, Zinc and any combination thereof.

A further object of the invention is to disclose a system for measuring element concentration in plant leaves. The aforesaid system comprises: (a) means for conditioning specimens of said leaves; (b) a NIR spectrometer configured for obtaining raw NIR datasets of said specimens; (c) an XRF spectrometer configured for obtaining raw count-per-second XRF datasets of said specimens; (d) an atomic emission spectrometer or an inductively coupled plasma optical emission spectrometer configured for obtaining analytical datasets of said specimens; (e) an assessing unit configured for assessing concentrations of minerals within said specimens on the basis of said count-per-second XRF, NIR and analytical datasets. The assessing unit is configured for obtaining white reference radiance datasets and normalizing said raw NIR datasets on the basis thereof and providing NIR reflectance datasets.

A further object of the invention is to disclose the means for conditioning specimens of said leaves comprising a dust washer configured for removing dust from said leave, a grinder configured for producing a fresh paste specimens from said leaves, a dryer configured for specimen dehydration, a weigh-scales configured for weighing dehydrated specimens and a device for chemically digesting said dehydrated specimens.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to understand the invention and to see how it may be implemented in practice, a plurality of embodiments is adapted to now be described, by way of non-limiting example only, with reference to the accompanying drawings, in which.

DETAILED DESCRIPTION OF THE INVENTION

Figure 1:
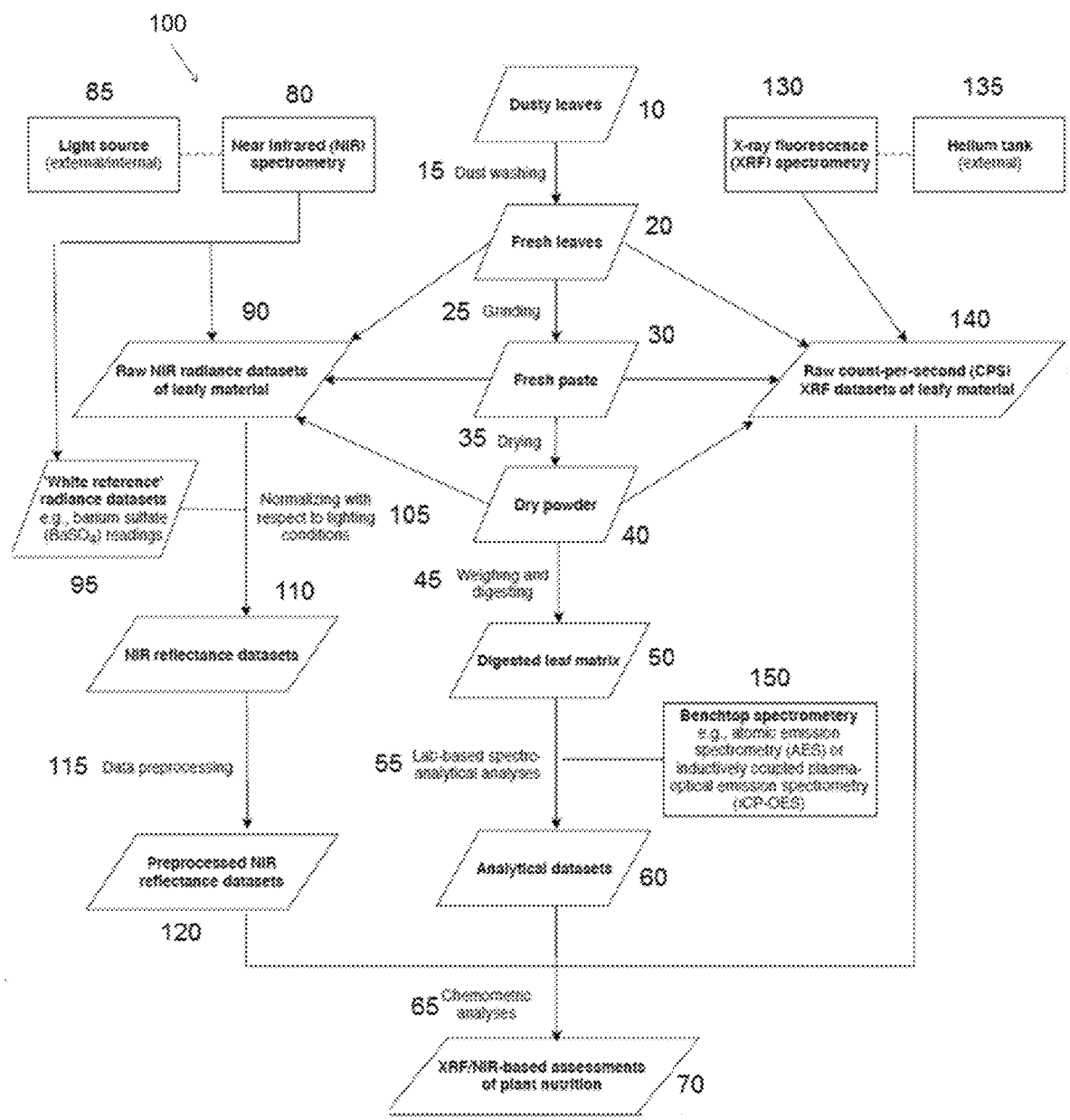
FIG. 1 is a schematic flowchart of a method of measuring element concentration in plant leaves.

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a method of measuring element concentration in plant leaves and a system for implementing the same.

Representative leafy material was collected from experiments of various plant species, growing seasons and environments, elements, and nutrient level gradients and presented in the results section. Once cut, the leaves were kept within a sealed container in order to minimize water loss until reaching the lab, wherein they were thoroughly washed from dust using distilled water. Thereafter, the material from each experiment was divided into three sample preparation groups of a similar nutrition range: (1) whole leaves; (2) whole leaves made into a homogenic fresh paste; and (3) whole leaves made into a homogenic dry powder. In the case of the fresh paste and dry powder forms, about 5 g of material was compacted into designated XRF or NIR measurement cups, pursuing a thickness of roughly 1.5 cm and an "infinitely-thick" density, which were sealed at their measuring-end using a 4 µm-thin polypropylene film. In this regard, it is important to note that the recent advances in pEDXRF technology no longer dictate the pressing of paste or powder into pellets or 'leaf discs'—a prevailing method in previous studies that aims to increase the uniformity and compactness of the sample—making sample preparation and measuring much easier, faster, comfortable, economical, repetitive and free from the use of binding agents. Unlike the fresh paste or dry powder forms, the intact leaves were compressed into a measuring cup with its center pressed against the film, as this location was of more interest to the analysis than others. At the end of every paste or whole leaf measurement, the fresh material was weighed (FW), completely oven-dried at 70° C., and then reweighed (DW) in order to calculate relative water content (RWC):

$$RWC(\%) = \frac{FW - DW}{FW} * 100 \qquad (1)$$

Finally, the dried material from all sample preparation forms was sent to the lab for reference, digestion-based analyses.

The XRF measurements were performed with an XL3t GOLDD+ (Thermo Fisher Scientific Inc., MA, USA) spectrometer that was filled with 99.9999% pure helium (He) gas to increase the sensitivity for lighter elements. The total measuring time for all macro- and micro-elements was 3 minutes, divided equally between the light ($Z<K$), low ($K \leq Z \leq$ chromium (Cr)), and main ($Z>Cr$) optimized filters to ensure stable count-per-second (CPS) readings and sufficiently low error levels. All measurements were done while the instrument was mounted into a designated radiation-protective stand and, thus, the sampling distance and area remained constant throughout all experiments.

The NIR measurements were performed with FieldSpec4 (Analytical Spectral Devices Inc., CO, USA) and USB-2000 (Ocean Optics Inc., FL, USA) spectrometers, using an external LS-1 Tungsten Halogen Light Source (Ocean Optics Inc., FL, USA). The samples were put in designated measuring cups, placed at an optimal distance from the measuring device, and their average energy flux reading ($E_{SAMPLE}$) was taken. Thereafter, the $E_{SAMPLE}$ values were normalized into a reflectance ($\rho$) base using 'white reference' readings ($E_{WR}$) of a WS-1-SL Diffuse Reflectance Standard (Ocean Optics, FL, USA) and dark current readings ($E_{DARK}$):

$$\rho(\%) = \frac{E_{SAMPLE} - E_{DARK}}{E_{WR} - E_{DARK}} * 100 \qquad (2)$$

All PLSR analyses were performed using the PLS_Toolbox (version 8.62; Eigenvector Research Inc., WA, USA) software, running under a MATLAB (version R2007a; The Mathworks Inc., MA, USA) environment. While pre-processing of the raw spectral data is considered a common practice in the literature and is the default option in various chemometric software (including preliminary steps of variable scaling, normalizing, centering, smoothing, etc.), it is important to note that the XRF regression models presented here were not based on any pre-processing step, and that pre-processing might not always be advantageous in spectral studies in general and in fluorescence studies in particular; this is likely due to the nature of the raw CPS data—often characterized by specific peaks of a meaningful signal surrounded by wavelengths of only background noise (e.g., heavier elements) or by low SNR values (e.g., lighter elements)—that is not apt for operations such as smoothing or scaling, which weaken the intensity of important wavelengths or strengthen the intensity of redundant ones, respectively. Regarding the NIR spectral pre-processing, however, the Savitzky-Golay algorithm was used to perform a high-pass; first and second derivative filters on the datasets. In order to avoid over-fitting, the calibration regressions were optimally constructed by selecting the lowest possible number of latent variables (LV) that explained most of the variation in both the spectra (predictor) and element concentration (predicted) blocks, and the models were then tested against cross-validations (Venetian Blinds) and independent predictions. The contribution degree of all X-ray and NIR wavelengths was finally assessed using the Variable Importance in Projection (VIP) measure, which reflects the weighted sum of squares of the PLS weights.

Reference is now made to FIG. 1 presenting a schematic flowchart of method 100 of measuring element concentration in plant leaves. Dusty leaves 10 are washed at step 15. Then, different specimens of the leaves are measured: fresh leaves 20, fresh paste 30 made by grinding 25 and dry powder 40 dried at step 35. The aforesaid specimens (20, 30 and 40) are tested by NIR spectrometer 80 provided with light source 85 and XRF spectrometer 130 provided with Helium tank 135. Raw NIR and XRF datasets 90 and 140, respectively, are obtained. In parallel with obtaining NIR datasets 90, white reference radiance datasets 95 are measured. Measuring of barium sulfate in order to obtain the aforesaid reference radiance datasets 95 is in the scope of the present invention. NIR datasets 90 are normalized (step 105) on the basis of reference radiance datasets 95 such that NIR reflectance datasets 110 are obtained. Preprocessing radiance datasets 95 at step 115 results in preprocessed NIR reflectance datasets 120. In parallel to the abovementioned operations, dry powder 40 is weighed and chemically digested (step 45) such that digested leaf matrix is obtained. Analytical datasets 60 are provided by means of lab-based spectral analyses 55. Benchtop spectrometry such as atomic emission spectrometry or inductively-coupled plasma optical emission spectrometry can be used. On the basis of chemometric analyses 65, XRF/NIR-based assessment 70 of plant nutrition can be carried out.

Figure 2:
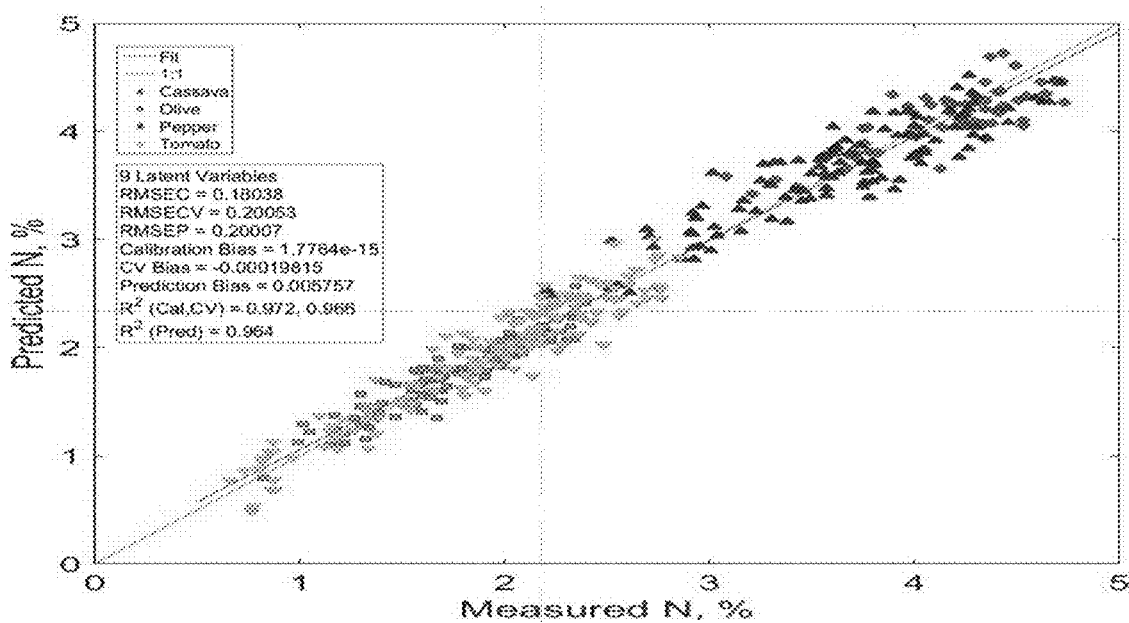
FIG. 2 is a graph of NIR-partial least squares regression calibration and prediction models for nitrogen (N) in dried leaf powder form.
Figure 3A:
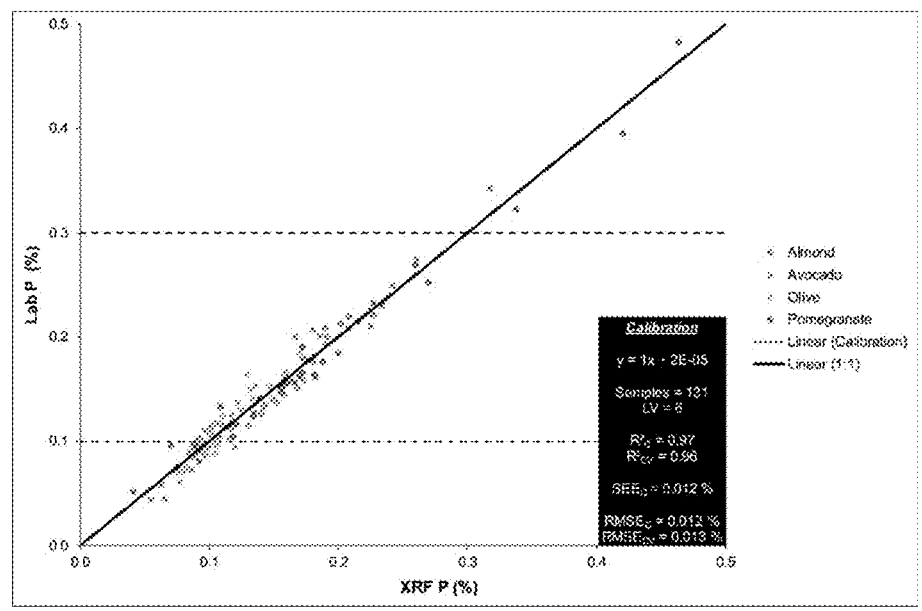
FIGS. 3a and 3b are graphs of XRF-partial least squares regression calibration and prediction models for phosphorus (P) in dry leaf powder form, respectively.
Figure 3B:
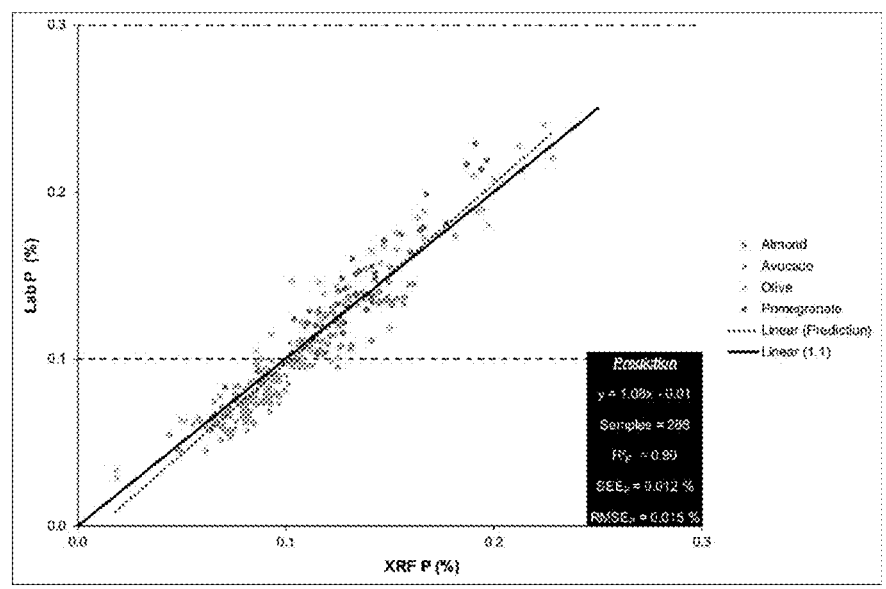
Figure 4A:
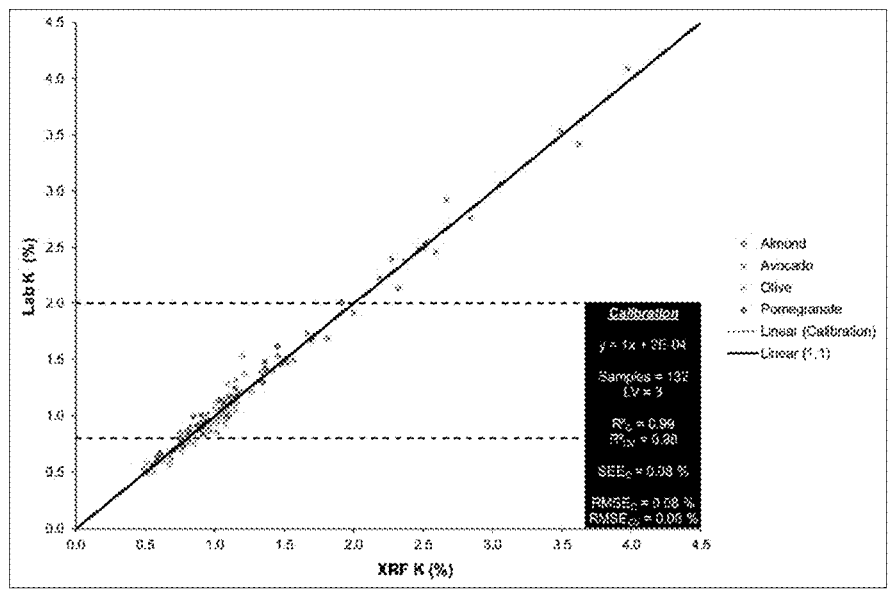
FIGS. 4a and 4b are graphs of XRF-partial least squares regression calibration and prediction models for potassium (K) in dry leaf powder form, respectively.
Figure 4B:
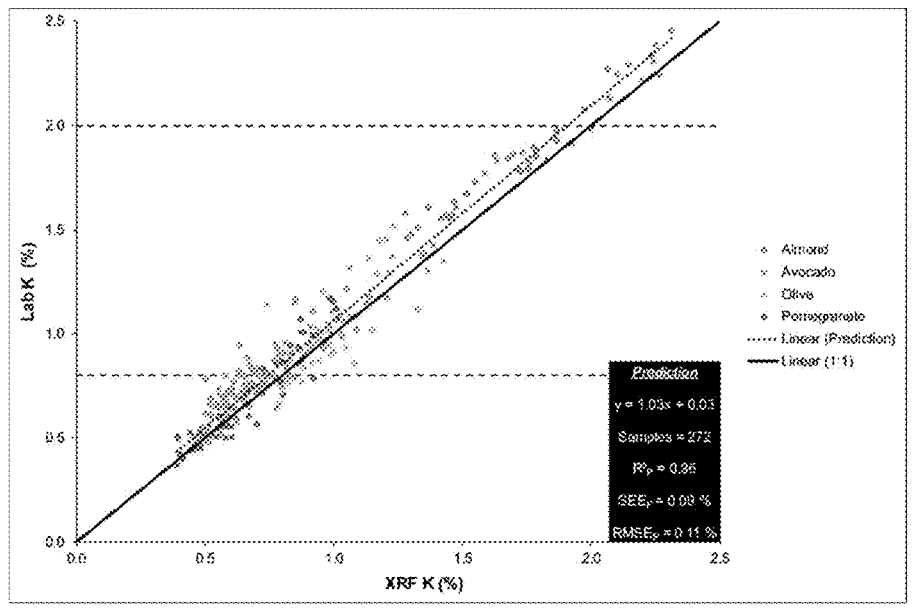
Figure 5A:
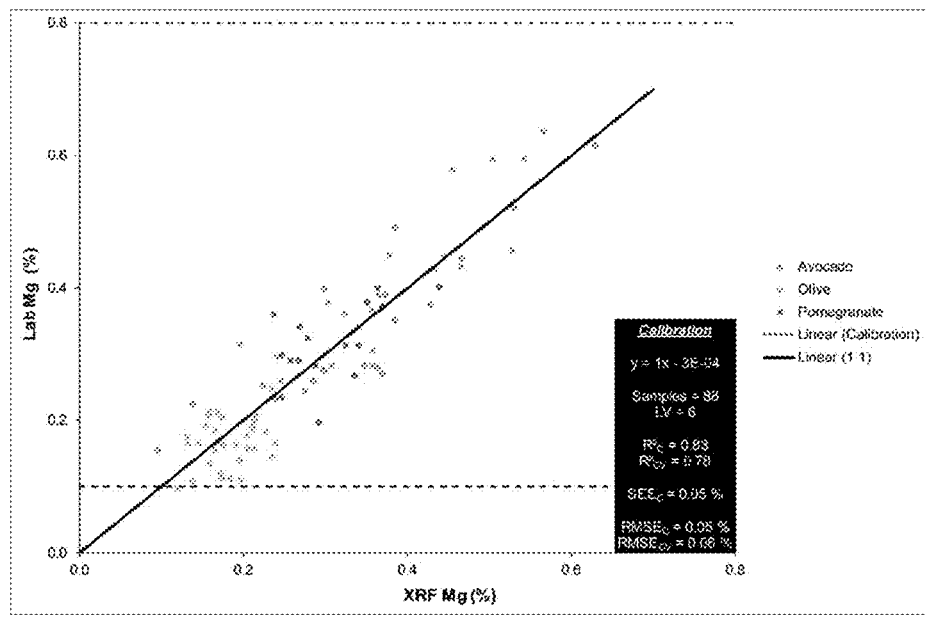
FIGS. 5a and 5b are graphs of XRF-partial least squares regression calibration and prediction models for magnesium (Mg) in dry leaf powder form, respectively.
Figure 5B:
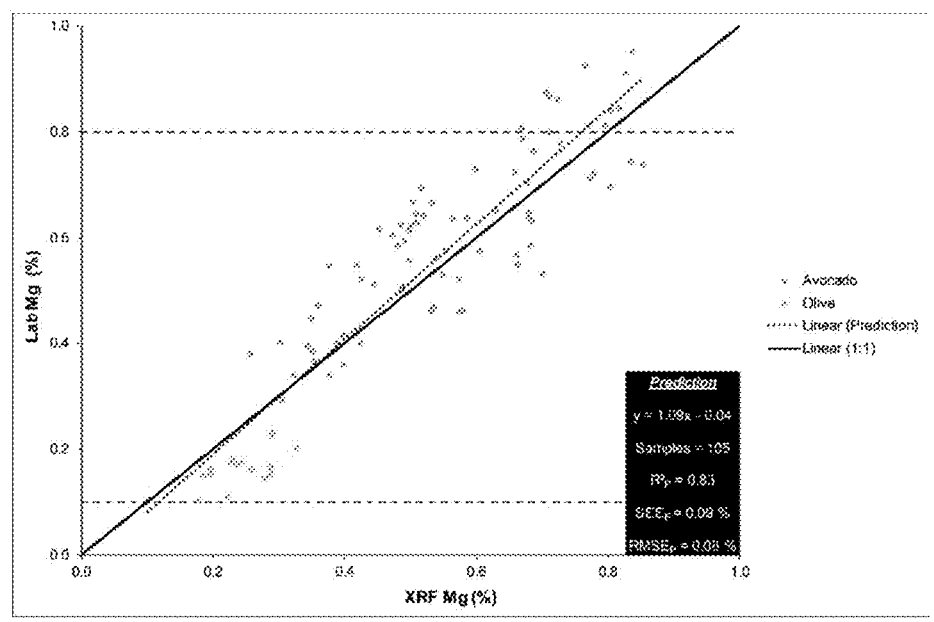
Figure 6A:
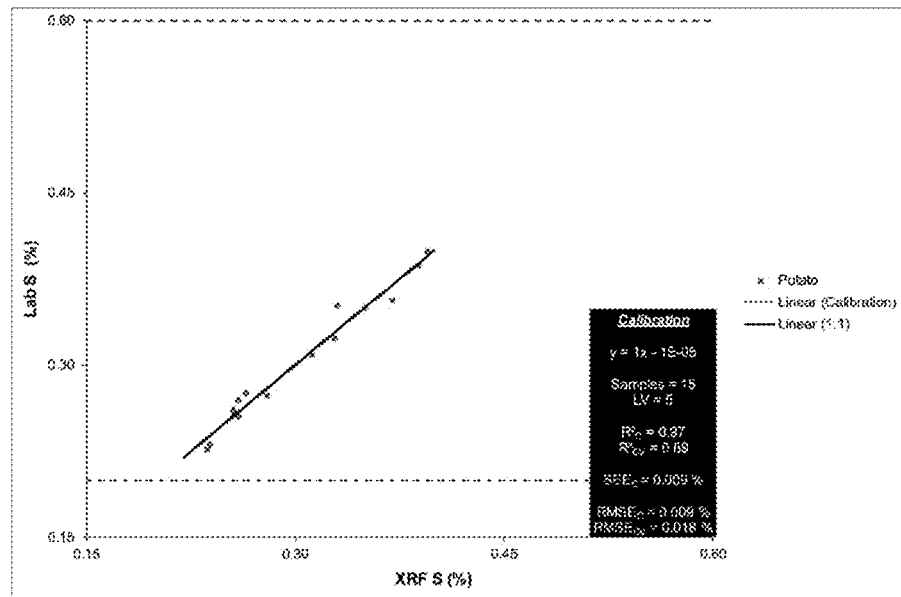
FIGS. 6a and 6b are graphs of XRF-partial least squares regression calibration and prediction models for sulfur (S) in dry leaf powder form, respectively.
Figure 6B:
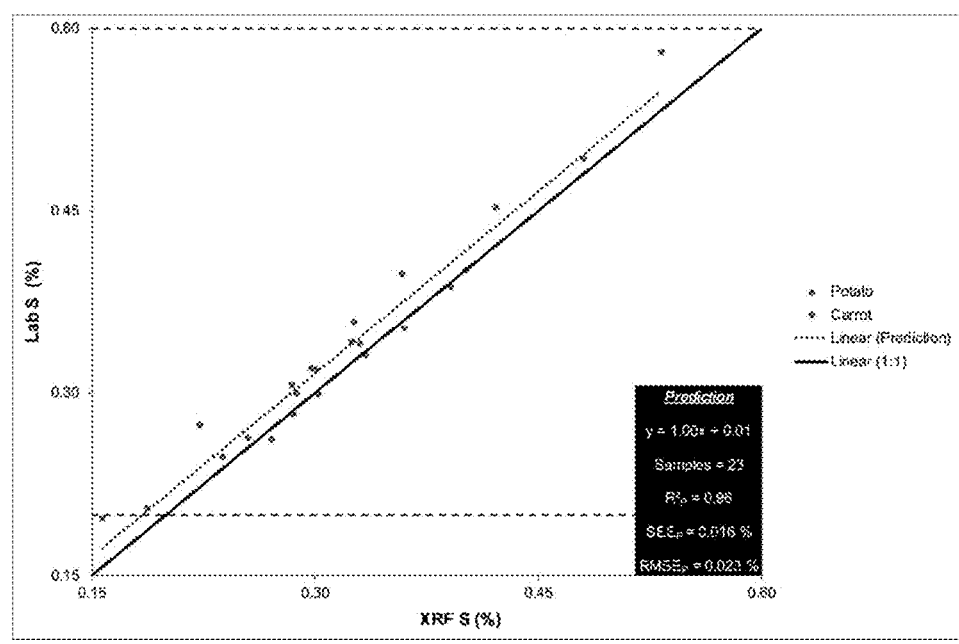
Figure 7A:
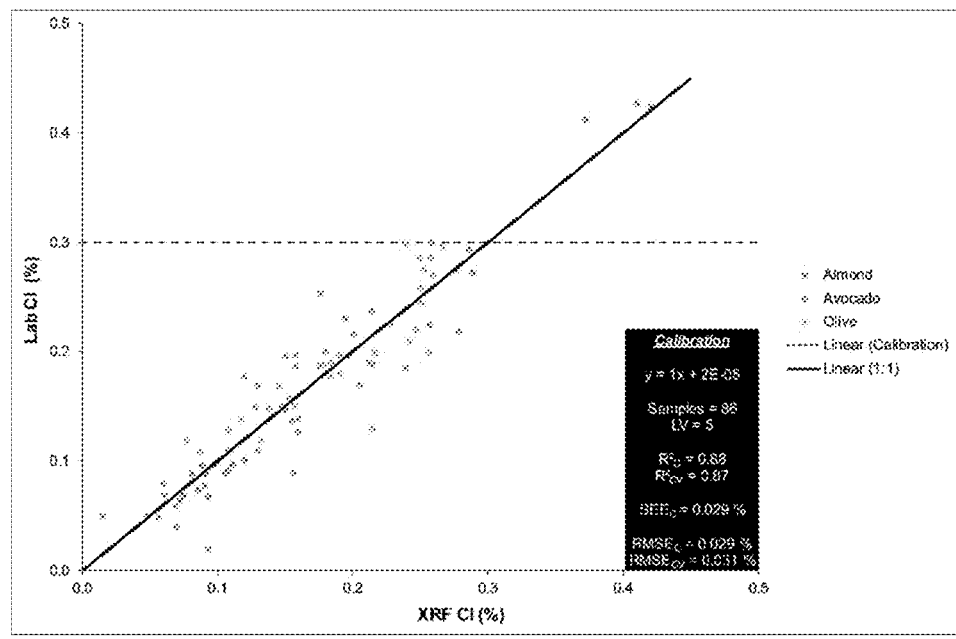
FIGS. 7a and 7b are graphs of XRF-partial least squares regression calibration and prediction models for chlorine (Cl) in dry leaf powder form, respectively.
Figure 7B:
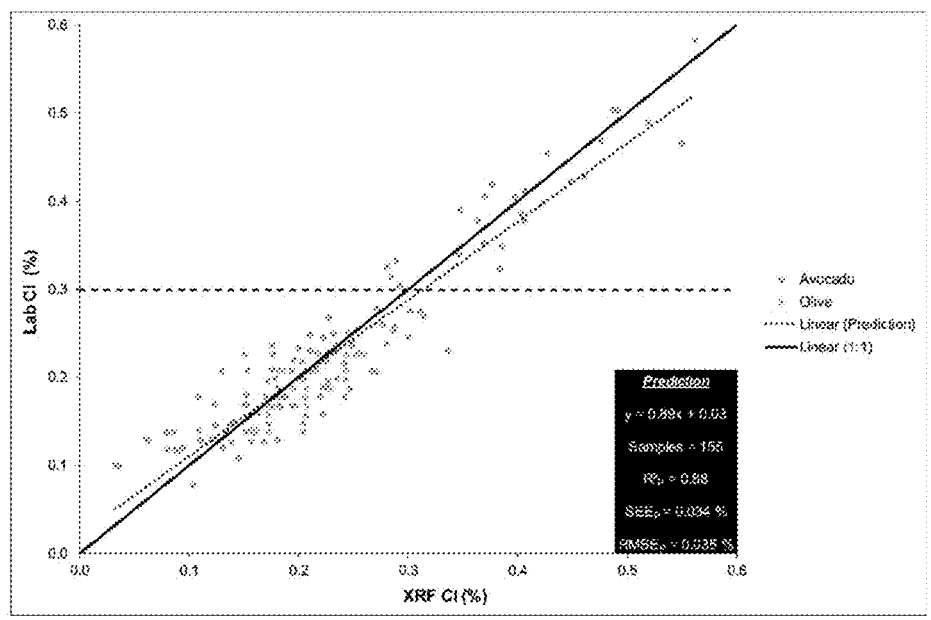
Figure 8A:
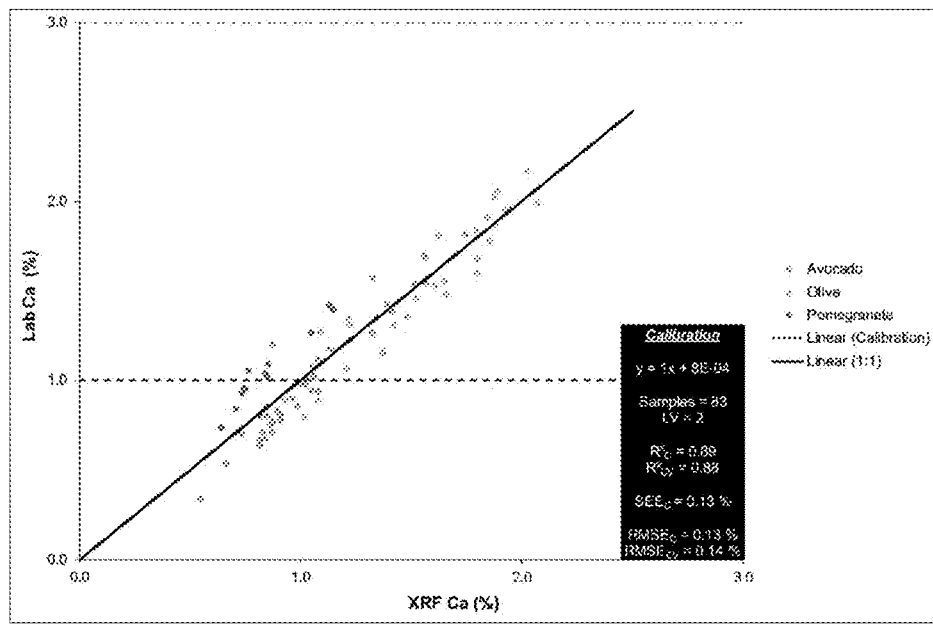
FIGS. 8a and 8b are graphs of XRF-partial least squares regression calibration and prediction models for calcium (Ca) in dry leaf powder form, respectively.
Figure 8B:
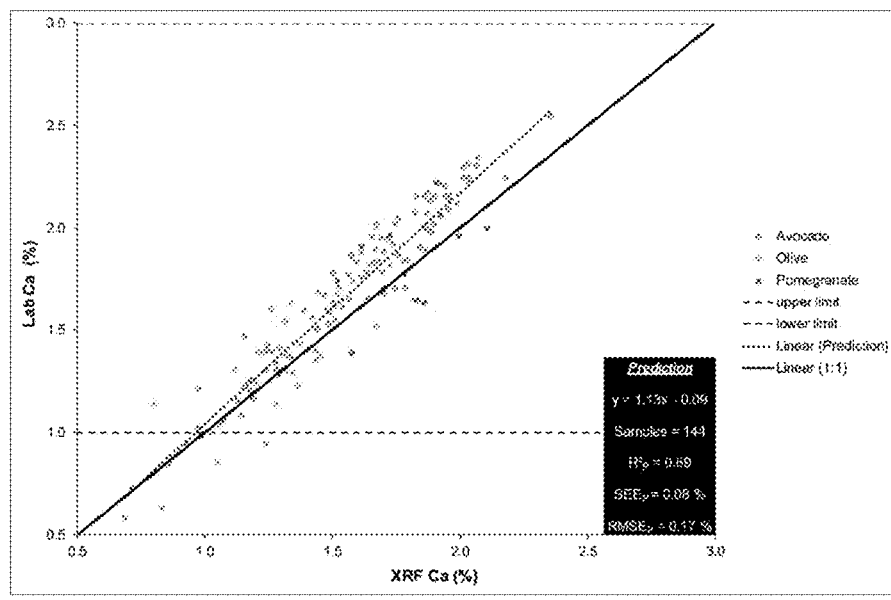
Figure 9A:
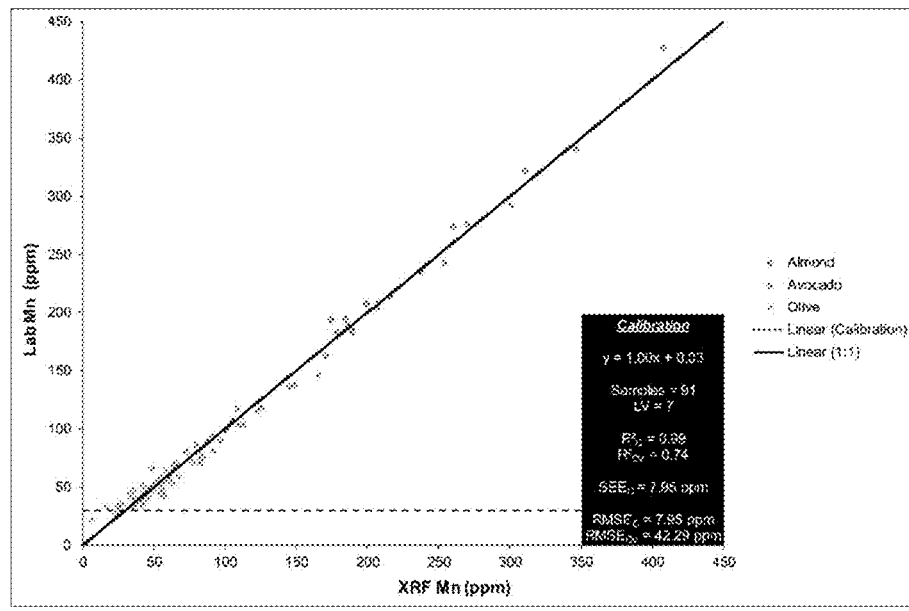
FIGS. 9a and 9b are graphs of XRF-partial least squares regression calibration and prediction models for manganese (Mn) in dry leaf powder form, respectively.
Figure 9B:
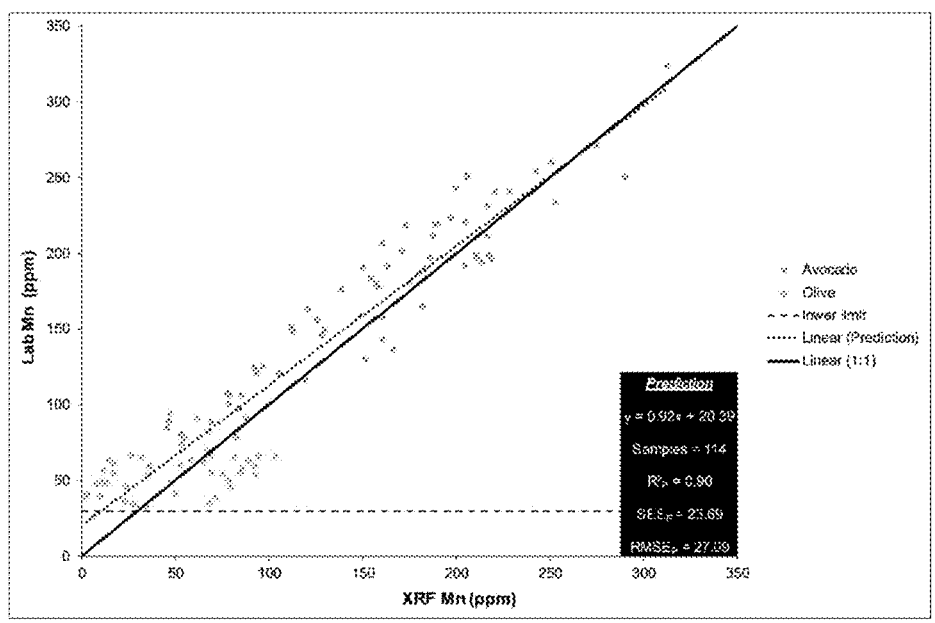
Figure 10A:
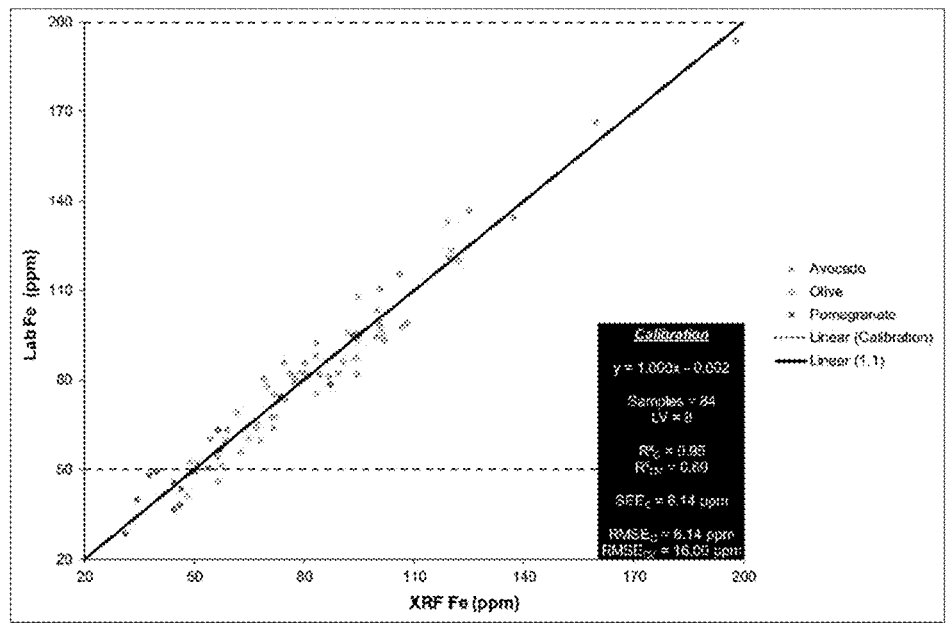
FIGS. 10a and 10b are graphs of XRF-partial least squares regression calibration models for iron (Fe) in dry leaf powder form, respectively.
Figure 10B:
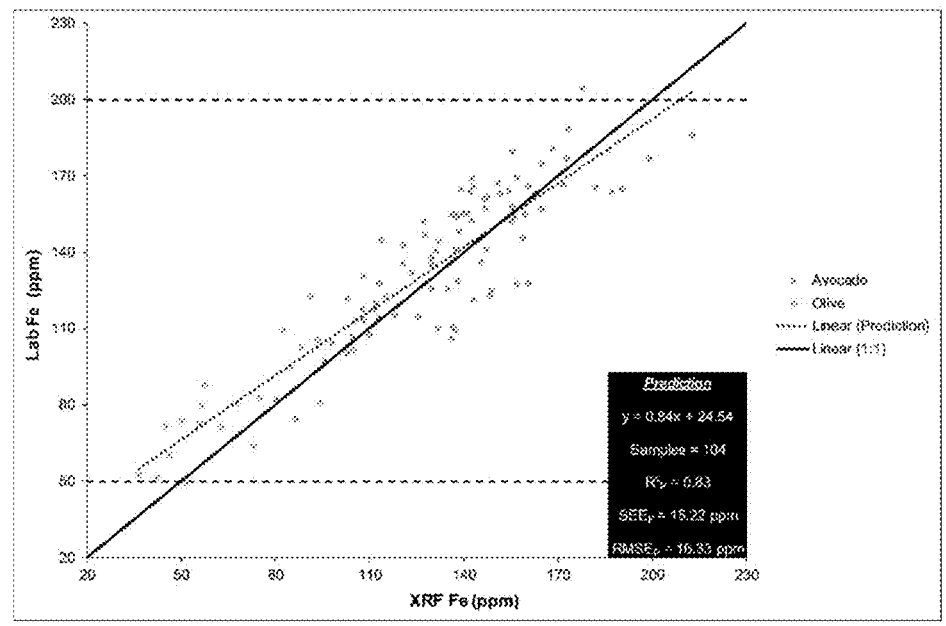
Figure 11A:
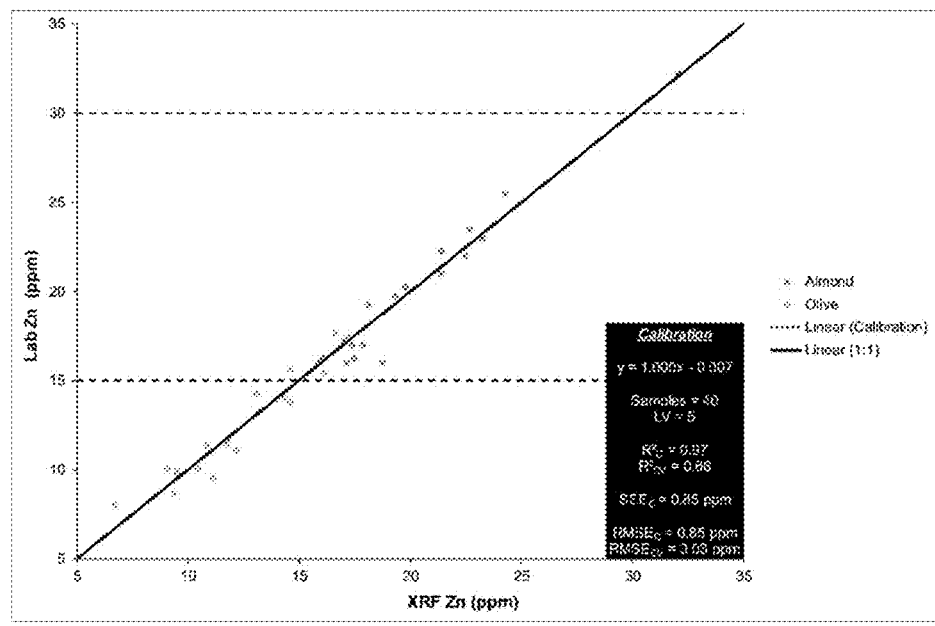
FIGS. 11a and 11b are graphs of XRF-partial least squares regression calibration and prediction models for zinc (Zn) in dry leaf powder form, respectively.
Figure 11B:
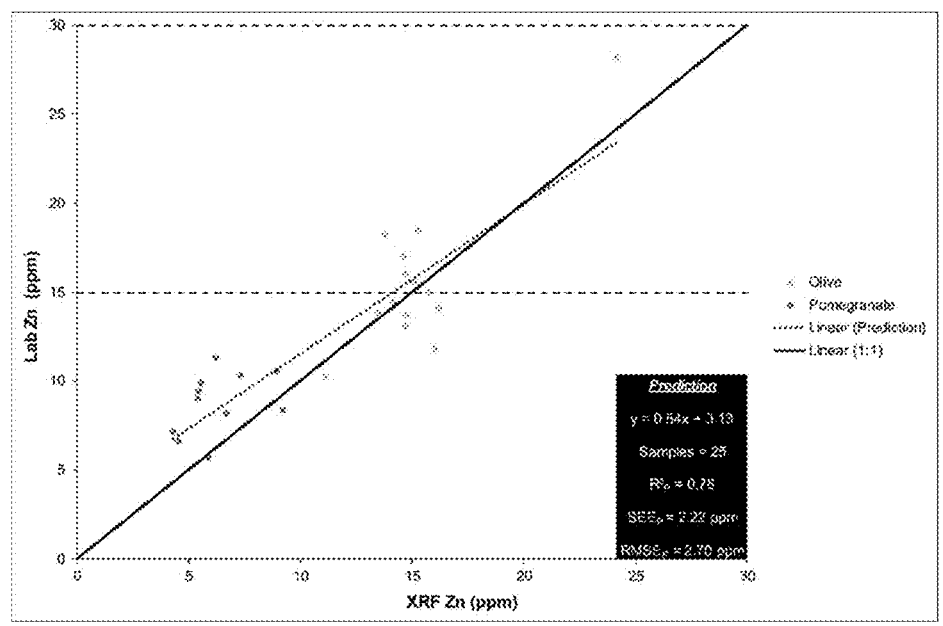

By applying the PLSR technique on the NIR reflectance signatures and the raw XRF (CPS) data, very strong and robust linear calibration models were created for prediction of dry leaf powder-based N (FIG. 2), P (FIG. 3) and K (FIG. 4). Specifically, the regressions were based on multiple species and hundreds of samples, spanned across wide nutritional gradients (covering the deficiency-adequacy-excess range of each element), characterized by a relatively low number of latent variables (LV), presenting extremely high coefficients of determination for the calibration ($R^2_C$) and cross-validation ($R^2_{CV}$) curves, and displaying very low standard errors of the estimate ($SEE_C$) and root mean squared errors ($RMSE_C$, $RMSE_{CV}$). Furthermore, the N, P and K calibration models were able to accurately predict new, independent datasets of different cultivars, growing environments and even larger proportions—showing high coefficients of determinations ($R^2_P$) and low standard errors of the estimate ($SEE_P$) and root mean squared errors ($RMSE_P$). In this regard, it is important to note the ability of the P model to accurately predict deficient values below 0.1%, which is both a common nutritional threshold for numerous plant species and the limit of detection (LOD) for many XRF instruments. Other than P and K, the XRF-PLSR combination was also very successful in predicting digestion-based measurements of other majorly-acquired nutrients, including Mg (FIG. 5), S (FIG. 6.), Cl (FIG. 7), and Ca (FIG. 8), of which the former element was especially encouraging due to its low Z and consequent noisy signal. In addition, not unlike the success of Mg, applying the PLSR method was also beneficial to the accurate monitoring of Mn (FIG. 9), Fe (FIG. 10) and Zn (FIG. 11)—minor-essential elements that produce low SNR values and, thus, cannot be monitored solely using an XRF spectrometer.

Figure 12:
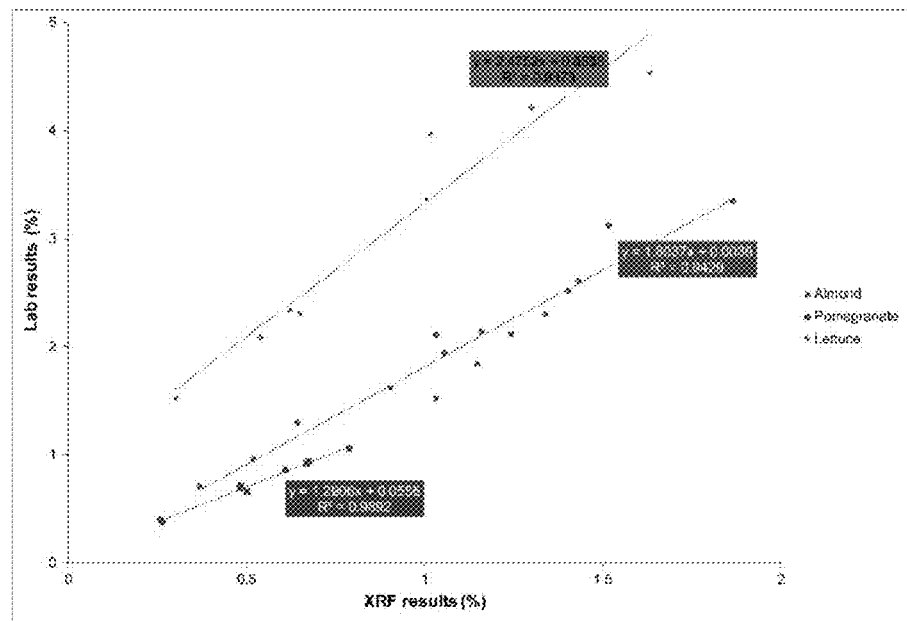
FIG. 12 is a graph of XRF calibration model for potassium (K) in fresh leaf paste form.
Figure 13:
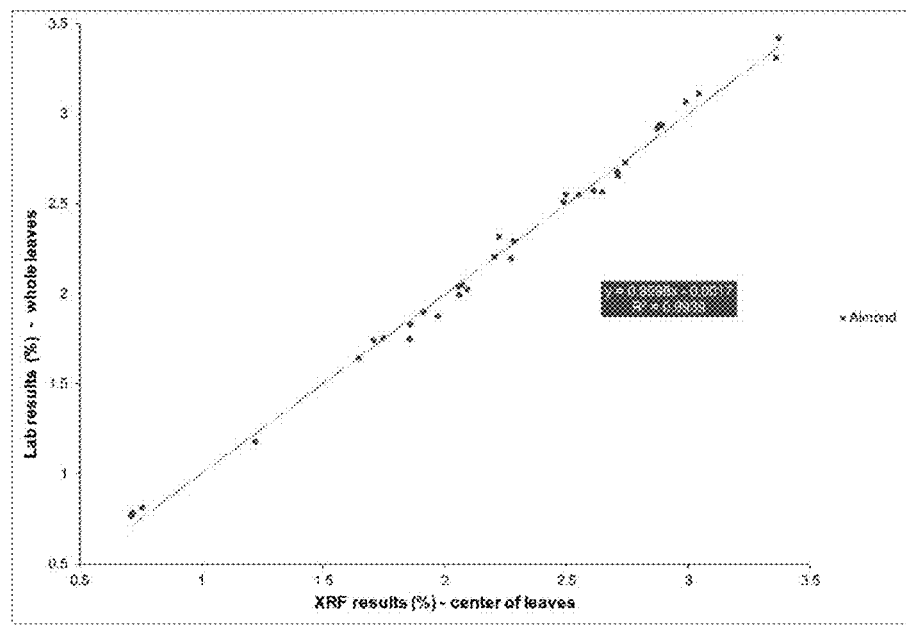
FIG. 13 is a graph of XRF-partial least squares regression calibration model for potassium (K) in whole intact leaf form.

Finally, despite leaf RWC-related interferences, strong K models were also created for the fresh paste form (FIG. 12) and even for whole, intact leaves (FIG. 13). These latter results are especially encouraging, as they were obtained during the course of preliminary trials, with the samples having RWC values >60%. Moreover, it should be noted that the experimental conditions of the whole, intact leaves trial were far-from-ideal, as the relatively loose contact between the leaf surface and the XRF sampling cup (see the methodology section) potentially introduced significant air atmosphere-interferences—unlike the cases of the dry leaf powder or the fresh leaf paste.

The invention claimed is:

1. A method of measuring element concentration in plant leaves; said method comprising steps of:
    gathering leaves of plants to be tested;
    conditioning specimens of said leaves;
    obtaining raw count-per-second XRF datasets of said specimens;
    obtaining raw NIR datasets of said specimens;
    obtaining white reference radiance datasets and normalizing said raw NIR datasets on the basis thereof;
    obtaining raw analytical datasets; and,
    assessing concentrations of minerals within said specimens on the basis of a correlation model between said count-per-second XRF, NIR and said analytical datasets;
    wherein said specimens of said leaves comprise material from fresh leaves; further wherein said method does not comprise any step of preprocessing said spectroscopy XRF datasets, further wherein said correlation model is a unified model adjusted for more than one species of plant.

2. The method according to claim 1, wherein said step of conditioning specimens of said leaves comprises dust washing of said leaves, grinding said leaves, drying ground leaves, weighing dried leaves, chemically digesting said dried leaves.

3. The method according to claim 1, wherein said step of assessing concentrations of minerals comprises a step of preprocessing normalized NIR datasets.

4. The method according to claim 1, wherein said step of obtaining raw count-per-second XRF datasets of said specimens is performed by means of an XRF spectrometer.

5. The method according to claim 4, wherein said step of obtaining raw count-per-second XRF is preceded by a step of filling said XRF spectrometer with helium gas.

6. The method according to claim 1, wherein said step of obtaining raw NIR datasets of said specimens is performed by means of a NIR spectrometer.

7. The method according to claim 1, wherein said step of obtaining analytical datasets is performed by an atomic emission spectrometer.

8. The method according to claim 1, wherein said step of obtaining analytical datasets is performed by an inductively coupled plasma optical emission spectrometer.

9. The method according to claim 1, wherein said step of assessing concentrations of minerals within said specimens comprises a mineral selected from the group consisting of Magnesium, Sulfur, Chlorine, Calcium, Manganese, Iron, Zinc and any combination thereof.

10. The method according to claim 1, wherein said material from fresh leaves comprises at least one member selected from the group consisting of fresh intact leaves and fresh leaf paste.

11. The method according to claim 1, wherein said correlation model facilitates correlation between levels of minerals in both fresh and dry materials.

* * * * *